US006713449B1

(12) United States Patent
Shibata et al.

(10) Patent No.: US 6,713,449 B1
(45) Date of Patent: Mar. 30, 2004

(54) E2F ACTIVITY INHIBITORY COMPOUNDS

(75) Inventors: Kenji Shibata, Tokyo (JP); Motoo Yamasaki, Tokyo (JP); Tetsuo Yoshida, Irving, TX (US); Tamio Mizukami, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/269,576

(22) PCT Filed: Sep. 26, 1997

(86) PCT No.: PCT/JP97/03442

§ 371 (c)(1),
(2), (4) Date: Mar. 30, 1999

(87) PCT Pub. No.: WO98/14474

PCT Pub. Date: Apr. 9, 1998

(30) Foreign Application Priority Data

Sep. 30, 1996 (JP) ............................................... 8-259432

(51) Int. Cl.[7] .......................... A61K 38/17; C07K 14/47
(52) U.S. Cl. .............................. 514/12; 514/14; 514/21; 530/324; 530/327; 530/350
(58) Field of Search ............................ 514/2, 8, 12, 13, 514/14, 21; 530/300, 324, 325, 326, 327, 350, 358, 395

(56) References Cited

U.S. PATENT DOCUMENTS

| 5,064,939 A | 11/1991 | Rivier et al. | 530/317 |
|---|---|---|---|
| 5,418,135 A | 5/1995 | Pang | 435/7.1 |
| 5,759,803 A | * 6/1998 | Kaelin, Jr. et al. | 435/69.1 |

OTHER PUBLICATIONS

Molecular and Cellular Biology, Chin–Lee Wu, vol. 15, No. 5, May 1995, pp. 2536–2546.
Genes & Development, Kristian Helin, 1993, pp. 1850–1861. vol. 7.
The EMBO Journal, vol. 11, No. 5, 1992, pp. 1797–1804.
Nature Biotechnology, Lasantha R. Bandara, vol. 15, Sep. 1997,, pp. 896–901.
Cell, Kristian Helin, vol. 70, Jul. 24, 1992, pp. 337–350.
Cell, William G. Kaelin, Jr., vol. 70, Jul. 24, 1992, pp. 351–364.
Mol. and Cell. Bio., M. Ivey–Hoyle, vol. 13, No. 12, Dec. 1993, pp. 7802–7812.
Mol. and Cell. Bio., J. A. Lees, vol. 13, No. 12, Dec. 1993, pp. 7813–7825.
Genes & Development, Roderick L. Beijersbergen, 1994, pp. 2680–2690. vol. 8.
Genes & Development, Doron Ginsberg, 1994, pp. 2665–2679. vol. 8.
Proc. Natl. Acad. Sci. USA, Claude Sardet, vol. 92, Mar. 1995, pp. 2403–2407.
Nature, Rowena Girling, vol. 362, Mar. 4, 1993, pp. 83–87.

\* cited by examiner

*Primary Examiner*—Jeffrey E. Russel
(74) *Attorney, Agent, or Firm*—Fitzpatrick, Cella, Harper & Scinto

(57) ABSTRACT

E2F-inhibiting compounds are represented by the formula: $R^1$—A—$R^2$ wherein A represents a peptide sequence comprising a partial amino acid sequence having at least 12 continuous residues in the sequence of the dimerization region or DNA binding region of the E2F family, which are useful as a therapeutic agent of diseases such as tumor and arteriosclerosis, for which abnormal cellular growth is implicated.

6 Claims, No Drawings

SEQUENCE LISTING

```
<160> NUMBER OF SEQ ID NOS: 27

<210> SEQ ID NO 1
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
<223> OTHER INFORMATION: Xaa at position 1 representing N-acetyl-L-
      leucine
<220> FEATURE:
<221> NAME/KEY: Modified-site
<222> LOCATION: 29
<223> OTHER INFORMATION: Xaa at position 29 representing L-alaninamide

<400> SEQUENCE: 1

Xaa Asn Trp Ala Ala Glu Val Leu Lys Val Gln Lys Arg Arg Ile Tyr
 1               5                  10                  15

Asp Ile Thr Asn Val Leu Glu Gly Ile Gln Leu Ile Xaa
             20                  25
```

```
<210> SEQ ID NO 2
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
<223> OTHER INFORMATION: Xaa at position 1 representing N-acetyl-L-
      valine
<220> FEATURE:
<221> NAME/KEY: Modified-site
<222> LOCATION: 15
<223> OTHER INFORMATION: Xaa at position 15 representing L-valinamide

<400> SEQUENCE: 2

Xaa Leu Lys Val Gln Lys Arg Arg Ile Tyr Asp Ile Thr Asn Xaa
 1               5                  10                  15

<210> SEQ ID NO 3
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
<223> OTHER INFORMATION: Xaa at position 1 representing N-acetyl-L-
      asparagine
<220> FEATURE:
<221> NAME/KEY: Modified-site
<222> LOCATION: 28
<223> OTHER INFORMATION: Xaa at position 28 representing L-serinamide

<400> SEQUENCE: 3

Xaa Glu Ser Ala Tyr Asp Gln Lys Asn Ile Arg Arg Val Tyr Asp
 1               5                  10                  15

Ala Leu Asn Val Leu Met Ala Met Asn Ile Ile Xaa
                20                  25

<210> SEQ ID NO 4
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
<223> OTHER INFORMATION: Xaa at position 1 representing N-acetyl-L-
      isoleucine
<220> FEATURE:
<221> NAME/KEY: Modified-site
<222> LOCATION: 15
<223> OTHER INFORMATION: Xaa at position 15 representing L-
      methioninamide

<400> SEQUENCE: 4

Xaa Arg Arg Arg Val Tyr Asp Ala Leu Asn Val Leu Met Ala Xaa
 1               5                  10                  15

<210> SEQ ID NO 5
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
```

```
<223> OTHER INFORMATION: Xaa at position 1 representing N-acetyl-L-
      alanine
<220> FEATURE:
<221> NAME/KEY: Modified-site
<222> LOCATION: 35
<223> OTHER INFORMATION: Xaa at position 35 representing L-leucinamide

<400> SEQUENCE: 5

Xaa Arg Gly Arg Gly Arg His Pro Gly Lys Gly Val Lys Ser Pro Gly
 1               5                  10                  15

Glu Arg Ser Arg Tyr Glu Thr Ser Leu Asn Leu Thr Thr Lys Arg Phe
            20                  25                  30

Leu Glu Xaa
        35

<210> SEQ ID NO 6
<211> LENGTH: 38
<212> TYPE: DNA
<213> ORGANISM: Artificial Sequence
<220> FEATURE:
<223> OTHER INFORMATION: Primer for recovery of cDNA

<400> SEQUENCE: 6
agagagaagc ttaaagcgtc atggccttgg ccggggcc                        38

<210> SEQ ID NO 7
<211> LENGTH: 26
<212> TYPE: DNA
<213> ORGANISM: Artificial Sequence
<220> FEATURE:
<223> OTHER INFORMATION: Primer for recovery of cDNA

<400> SEQUENCE: 7
ttctgcacct tcagcacctc ggcagc                                     26

<210> SEQ ID NO 8
<211> LENGTH: 26
<212> TYPE: DNA
<213> ORGANISM: Artificial Sequence
<220> FEATURE:
<223> OTHER INFORMATION: Primer for recovery of cDNA

<400> SEQUENCE: 8
accaagcgct tcctggagct gctgag                                     26

<210> SEQ ID NO 9
<211> LENGTH: 26
<212> TYPE: DNA
<213> ORGANISM: Artificial Sequence
<220> FEATURE:
<223> OTHER INFORMATION: Primer for recovery of cDNA

<400> SEQUENCE: 9
ggaaaccctg gtacctccaa gccctg                                     26

<210> SEQ ID NO 10
<211> LENGTH: 33
<212> TYPE: DNA
<213> ORGANISM: Artificial Sequence
<220> FEATURE:
<223> OTHER INFORMATION: Primer for PCR amplification

<400> SEQUENCE: 10
ccacggatcc ccagcactca ctttgcctct cag                             33
```

<210> SEQ ID NO 11
<211> LENGTH: 34
<212> TYPE: DNA
<213> ORGANISM: Artificial Sequence
<220> FEATURE:
<223> OTHER INFORMATION: Primer for PCR amplification

<400> SEQUENCE: 11
ctgcgaattc taccggtttc tctgcaccag gttc                               34

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide for gel-shift experiment

<400> SEQUENCE: 12
atttaagttt cgcgcccttt ctcaa                                         25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide for gel-shift experiment

<400> SEQUENCE: 13
ttgagaaagg gcgcgaaact taaat                                         25

<210> SEQ ID NO 14
<211> LENGTH: 30
<212> TYPE: DNA
<213> ORGANISM: Artificial Sequence
<220> FEATURE:
<223> OTHER INFORMATION: Primer for cloning human cdc2 promoter

<400> SEQUENCE: 14
ctatacactc ctaaccctaa gtattagaag                                    30

<210> SEQ ID NO 15
<211> LENGTH: 28
<212> TYPE: DNA
<213> ORGANISM: Artificial Sequence
<220> FEATURE:
<223> OTHER INFORMATION: Primer for cloning human cdc2 promoter

<400> SEQUENCE: 15
agctacaaca acgcgtcgct ctccgctc                                      28

<210> SEQ ID NO 16
<211> LENGTH: 22
<212> TYPE: DNA
<213> ORGANISM: Artificial Sequence
<220> FEATURE:
<223> OTHER INFORMATION: Fragment of reporter

<400> SEQUENCE: 16
tcgagcccgg gggtaccgca tg                                            22

<210> SEQ ID NO 17
<211> LENGTH: 14
<212> TYPE: DNA
<213> ORGANISM: Artificial Sequence
<220> FEATURE:
<223> OTHER INFORMATION: Fragment of reporter

```
<400> SEQUENCE: 17
cggtaccccc gggc                                                    14

<210> SEQ ID NO 18
<211> LENGTH: 60
<212> TYPE: DNA
<213> ORGANISM: Artificial Sequence
<220> FEATURE:
<223> OTHER INFORMATION: Fragment of reporter

<400> SEQUENCE: 18
tcgagcttgg cgggaaactt ggcgggaaac ttggcgggaa acttggcggg            50
aaagtcgacg                                                         60

<210> SEQ ID NO 19
<211> LENGTH: 60
<212> TYPE: DNA
<213> ORGANISM: Artificial Sequence
<220> FEATURE:
<223> OTHER INFORMATION: Fragment of reporter

<400> SEQUENCE: 19
gtaccgtcga ctttcccgcc aagtttcccg ccaagtttcc cgccaagttt            50
cccgccaagc                                                         60

<210> SEQ ID NO 20
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
<223> OTHER INFORMATION: Xaa at position 1 representing N-lauroyl-L-
      leucine
<220> FEATURE:
<221> NAME/KEY: Modified-site
<222> LOCATION: 29
<223> OTHER INFORMATION: Xaa at position 29 representing L-alaninamide

<400> SEQUENCE: 20

Xaa Asn Trp Ala Ala Glu Val Leu Lys Val Gln Lys Arg Arg Ile Tyr
  1               5                  10                  15

Asp Ile Thr Asn Val Leu Glu Gly Ile Gln Leu Ile Xaa
             20                  25

<210> SEQ ID NO 21
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1
<223> OTHER INFORMATION: Xaa at position 1 representing N-lauryl-L-
      asparagine
<220> FEATURE:
<221> NAME/KEY: Modified-site
<222> LOCATION: 28
<223> OTHER INFORMATION: Xaa at position 28 representing L-serinamide

<400> SEQUENCE: 21

Xaa Glu Ser Ala Tyr Asp Gln Lys Asn Ile Arg Arg Arg Val Tyr Asp
  1               5                  10                  15
```

```
Ala Leu Asn Val Leu Met Ala Met Asn Ile Ile Xaa
            20                  25

<210> SEQ ID NO 22
<211> LENGTH: 28
<212> TYPE: PRT
<213> ORGANISM: Artificial Sequence
<220> FEATURE:
<223> OTHER INFORMATION: Synthetic

<400> SEQUENCE: 22

Asn Glu Ser Ala Tyr Asp Gln Lys Asn Ile Arg Arg Arg Val Tyr
 1               5                  10                  15

Asp Ala Leu Asn Val Leu Met Ala Met Asn Ile Ile Ser
            20                  25

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Ile Arg Arg Arg Val Tyr Asp Ala Leu Asn Val Leu Met Ala Met
 1               5                  10                  15

<210> SEQ ID NO 24
<211> LENGTH: 28
<212> TYPE: PRT
<213> ORGANISM: Artificial Sequence
<220> FEATURE:
<223> OTHER INFORMATION: Synthetic

<400> SEQUENCE: 24

Asn Glu Ser Ala Tyr Asp Gln Lys Asn Ile Arg Arg Arg Val Tyr
 1               5                  10                  15

Asp Ala Leu Asn Val Leu Met Ala Met Asn Ile Ile Ser
            20                  25

<210> SEQ ID NO 25
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1-9 and 22-29
<223> OTHER INFORMATION: any one or all of amino acids 1-9 and 22-29 may
      be present or absent
<220> FEATURE:
<221> NAME/KEY: Modified-site
<222> LOCATION: 1, 8, 27 and 28
<223> OTHER INFORMATION: Xaa at positions 1, 8, 27 and 28 independently
      represent Leu or Ile
<220> FEATURE:
<221> NAME/KEY: Modified-site
<222> LOCATION: 2
<223> OTHER INFORMATION: Xaa at position 2 represents Asn or Lys
<220> FEATURE:
<221> NAME/KEY: Modified-site
<222> LOCATION: 3
<223> OTHER INFORMATION: Xaa at position 3 represents Trp, Lys, Leu, Ala
      or Glu
<220> FEATURE:
<221> NAME/KEY: Modified-site
<222> LOCATION: 5
<223> OTHER INFORMATION: Xaa at position 5 represents Ala or Ser
<220> FEATURE:
```

```
<221> NAME/KEY: Modified-site
<222> LOCATION: 6
<223> OTHER INFORMATION: Xaa at position 6 represents Glu, Asp or Asn
<220> FEATURE:
<221> NAME/KEY: Modified-site
<222> LOCATION: 7
<223> OTHER INFORMATION: Xaa at position 7 represents Val, Thr or Arg
<220> FEATURE:
<221> NAME/KEY: Modified-site
<222> LOCATION: 9
<223> OTHER INFORMATION: Xaa at position 9 represents Lys, Asp, Ala or
      His
<220> FEATURE:
<221> NAME/KEY: Modified-site
<222> LOCATION: 26
<223> OTHER INFORMATION: Xaa at position 26 represents Gln, His, Gly,
      Asp or Asn
<220> FEATURE:
<221> NAME/KEY: Modified-site
<222> LOCATION: 29
<223> OTHER INFORMATION: Xaa at position 29 represents Ala, Arg, Lys or
      Glu

<400> SEQUENCE: 25

Xaa Xaa Xaa Ala Xaa Xaa Xaa Xaa Xaa Val Gln Lys Arg Arg Ile
 1               5                  10                  15

Tyr Asp Ile Thr Asn Val Leu Glu Gly Ile Xaa Xaa Xaa Xaa
                20                  25

<210> SEQ ID NO 26
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1-10 and 26-29
<223> OTHER INFORMATION: any one or all of amino acids 1-10 and 26-29
      may be present or absent
<220> FEATURE:
<221> NAME/KEY: Modified-site
<222> LOCATION: 1
<223> OTHER INFORMATION: Xaa at position 1 represents Asn, Thr, Ala or
      Tyr
<220> FEATURE:
<221> NAME/KEY: Modified-site
<222> LOCATION: 2
<223> OTHER INFORMATION: Xaa at position 2 represents Glu or Asp
<220> FEATURE:
<221> NAME/KEY: Modified-site
<222> LOCATION: 3
<223> OTHER INFORMATION: Xaa at position 3 represents Ser or Asn
<220> FEATURE:
<221> NAME/KEY: Modified-site
<222> LOCATION: 5
<223> OTHER INFORMATION: Xaa at position 5 represents Ala or Asn
<220> FEATURE:
<221> NAME/KEY: Modified-site
<222> LOCATION: 6
<223> OTHER INFORMATION: Xaa at position 6 represents Tyr or Cys
<220> FEATURE:
<221> NAME/KEY: Modified-site
<222> LOCATION: 9
<223> OTHER INFORMATION: Xaa at position 9 represents Lys or Glu
<220> FEATURE:
<221> NAME/KEY: Modified-site
<222> LOCATION: 25
<223> OTHER INFORMATION: Xaa at position 25 represents Met or Ile
<220> FEATURE:
<221> NAME/KEY: Modified-site
<222> LOCATION: 27
<223> OTHER INFORMATION: Xaa at position 27 represents Ile or Val
```

<400> SEQUENCE: 26

Xaa Xaa Xaa Gln Xaa Xaa Asp Gln Xaa Asn Ile Arg Arg Arg Val
 1               5                   10                  15

Tyr Asp Ala Leu Asn Val Leu Met Ala Xaa Asn Xaa Ile Ser
                20                  25

<210> SEQ ID NO 27
<211> LENGTH: 41
<212> TYPE: PRT
<213> ORGANISM: Artificial Sequence
<220> FEATURE:
<223> OTHER INFORMATION: Synthetic
<220> FEATURE:
<221> NAME/KEY: Modified-site
<222> LOCATION: 1-25, 27-29, 32, 34, 36, 37, 39 and 40
<223> OTHER INFORMATION: any one or all of amino acids 1-25, 27-29,
      32, 34, 36, 37, 39 and 40 may be present or absent
<220> FEATURE:
<221> NAME/KEY: Modified-site
<222> LOCATION: 1
<223> OTHER INFORMATION: Xaa at position 1 represents Ala, Phe or Pro
<220> FEATURE:
<221> NAME/KEY: Modified-site
<222> LOCATION: 2
<223> OTHER INFORMATION: Xaa at position 2 represents Arg, Lys or Gln
<220> FEATURE:
<221> NAME/KEY: Modified-site
<222> LOCATION: 3, 15 and 21
<223> OTHER INFORMATION: Xaa at positions 3, 15 and 21 independently
      represent Gly or Pro
<220> FEATURE:
<221> NAME/KEY: Modified-site
<222> LOCATION: 4
<223> OTHER INFORMATION: Xaa at position 4 represents Arg, Lys, Met or
      Pro
<220> FEATURE:
<221> NAME/KEY: Modified-site
<222> LOCATION: 5
<223> OTHER INFORMATION: Xaa at position 5 represents Gly, Cys, Ala or
      Gln
<220> FEATURE:
<221> NAME/KEY: Modified-site
<222> LOCATION: 6
<223> OTHER INFORMATION: Xaa at position 6 represents Ala, Arg or Glu
<220> FEATURE:
<221> NAME/KEY: Modified-site
<222> LOCATION: 7
<223> OTHER INFORMATION: Xaa at position 7 represents Ala, Ile or Gln
<220> FEATURE:
<221> NAME/KEY: Modified-site
<222> LOCATION: 8
<223> OTHER INFORMATION: Xaa at position 8 represents Ala, Gly or Arg
<220> FEATURE:
<221> NAME/KEY: Modified-site
<222> LOCATION: 9
<223> OTHER INFORMATION: Xaa at position 9 represents Leu, Val or Pro
<220> FEATURE:
<221> NAME/KEY: Modified-site
<222> LOCATION: 10
<223> OTHER INFORMATION: Xaa at position 10 represents Asp, Arg or Gln
<220> FEATURE:
<221> NAME/KEY: Modified-site
<222> LOCATION: 11
<223> OTHER INFORMATION: Xaa at position 11 represents Gly, Ser, Ala or
      Pro
<220> FEATURE:
<221> NAME/KEY: Modified-site
<222> LOCATION: 12
<223> OTHER INFORMATION: Xaa at position 12 represents Leu or Pro
<220> FEATURE:
<221> NAME/KEY: Modified-site
<222> LOCATION: 13
<223> OTHER INFORMATION: Xaa at position 13 represents Asp, His or Pro
<220> FEATURE:
<221> NAME/KEY: Modified-site
<222> LOCATION: 14

<223> OTHER INFORMATION: Xaa at position 14 represents Ser or Pro
<220> FEATURE:
<221> NAME/KEY: Modified-site
<222> LOCATION: 16
<223> OTHER INFORMATION: Xaa at position 16 represents Gln or Lys
<220> FEATURE:
<221> NAME/KEY: Modified-site
<222> LOCATION: 17
<223> OTHER INFORMATION: Xaa at position 17 represents Gly, Thr or Leu
<220> FEATURE:
<221> NAME/KEY: Modified-site
<222> LOCATION: 18
<223> OTHER INFORMATION: Xaa at position 18 represents Gly, Pro or Val
<220> FEATURE:
<221> NAME/KEY: Modified-site
<222> LOCATION: 19
<223> OTHER INFORMATION: Xaa at position 19 represents Gly or Lys
<220> FEATURE:
<221> NAME/KEY: Modified-site
<222> LOCATION: 20
<223> OTHER INFORMATION: Xaa at position 20 represents Ala or Ser
<220> FEATURE:
<221> NAME/KEY: Modified-site
<222> LOCATION: 22
<223> OTHER INFORMATION: Xaa at position 22 represents Gly or Ser
<220> FEATURE:
<221> NAME/KEY: Modified-site
<222> LOCATION: 23
<223> OTHER INFORMATION: Xaa at position 23 represents Gly, Glu or Thr
<220> FEATURE:
<221> NAME/KEY: Modified-site
<222> LOCATION: 24
<223> OTHER INFORMATION: Xaa at position 24 represents Arg, Lys, Ser or
    Pro
<220> FEATURE:
<221> NAME/KEY: Modified-site
<222> LOCATION: 25
<223> OTHER INFORMATION: Xaa at position 25 represents Ser or Thr
<220> FEATURE:
<221> NAME/KEY: Modified-site
<222> LOCATION: 27
<223> OTHER INFORMATION: Xaa at position 27 represents His or Tyr
<220> FEATURE:
<221> NAME/KEY: Modified-site
<222> LOCATION: 28
<223> OTHER INFORMATION: Xaa at position 28 represents Asp or Glu
<220> FEATURE:
<221> NAME/KEY: Modified-site
<222> LOCATION: 29 and 36
<223> OTHER INFORMATION: Xaa at positions 29 and 36 independently
    represent Lys or Thr
<220> FEATURE:
<221> NAME/KEY: Modified-site
<222> LOCATION: 32
<223> OTHER INFORMATION: Xaa at position 32 represents Gly or Asn
<220> FEATURE:
<221> NAME/KEY: Modified-site
<222> LOCATION: 34
<223> OTHER INFORMATION: Xaa at position 34 represents Leu or Thr
<220> FEATURE:
<221> NAME/KEY: Modified-site
<222> LOCATION: 37
<223> OTHER INFORMATION: Xaa at position 37 represents Arg or Lys
<220> FEATURE:
<221> NAME/KEY: Modified-site
<222> LOCATION: 39
<223> OTHER INFORMATION: Xaa at position 39 represents Ile, Leu or Val
<220> FEATURE:
<221> NAME/KEY: Modified-site
<222> LOCATION: 40
<223> OTHER INFORMATION: Xaa at position 40 represents Glu, Gln, Ser or
    Tyr

<400> SEQUENCE: 27

Xaa Xaa Xaa Xaa Xaa Xaa Xaa Xaa Xaa Xaa Xaa Xaa Xaa Xaa Xaa
 1               5                  10                  15

```
-continued

Xaa Xaa Xaa Xaa Xaa Xaa Xaa Xaa Xaa Xaa Arg Xaa Xaa Xaa Ser
                20                  25                  30

Leu Xaa Leu Xaa Thr Xaa Xaa Phe Xaa Xaa Leu
         35              40
```

E2F ACTIVITY INHIBITORY COMPOUNDS

TECHNICAL FIELD

The present invention relates to a novel peptide useful as a therapeutic agent of diseases such as tumor and arteriosclerosis, for which cellular abnormal growth is responsible, by inhibiting the activity of a transcription factor E2F which regulates the transcription of gene groups involved in the progress of cell cycle to thereby suppress cell growth.

BACKGROUND ART

E2F is a transcription factor of importance for the transcription of a great number of genes involved in the progress of cell cycle and serves as a target protein of tumor suppression gene product Rb [EMBO J., 9, 2179 (1990); Cell, 65, 1053 (1991)]. As proteins comprising E2F, E2F family and DP family have been known. Up to now, five molecules of the E2F family, namely E2F 1 to 5 have been identified, while two molecules of the DP family, namely DP1 and 2, have also been identified. It has been believed that the out of control expression or activity of E2F is deeply involved in the carcinogenesis of a great number of cells [Science, 258, 424 (1992); Trends in Biological Science, 19, 108 (1994)]. It has also been reported that the inhibition of the transcriptional activity of E2F can suppress the growth of smooth muscle cells, which works as the cause of arteriosclerosis [Proc. Natl. Acad. Sci. USA., 92, 5855 (1995)]. Thus, the substance suppressing the E2F activity is useful as a therapeutic agent of tumor or diseases involving the abnormal growth of smooth muscle cells or the like, such as arteriosclerosis. Additionally, the substance may also be effective widely for autoimmune diseases which are exacerbated due to the growth of synovial cell, such as chronic rheumatoid arthritis, or diseases occurring because of the abnormal growth of mesangium cell, such as nephropathy. As to E2F suppressing agents, nucleic acid based compounds have been known, including antisense RNA [Cancer Res., 54, 1402 (1994)] and decoy based on the E2F binding sequence DNA [Proc. Natl. Acad. Sci. USA., 92, 5855 (1995)]. However, no peptides have been known yet as such suppressing agents.

DISCLOSURE OF THE INVENTION

In accordance with the present invention, it is provided a compound represented by the general formula (I);

$$R^1\text{—A—}R^2 \qquad (I)$$

(wherein $R^1$ represents substituted or unsubstituted alkanoyl, substituted or unsubstituted aroyl, substituted or unsubstituted heteroarylcarbonyl, substituted or unsubstituted alkoxycarbonyl, substituted or unsubstituted aryloxycarbonyl, substituted or , unsubstituted heteroaryloxycarbonyl or a hydrogen atom; $R^2$ represents hydroxy, substituted or unsubstituted alkoxy, or substituted or unsubstituted amino; and A represents a peptide sequence comprising a partial amino acid sequence having at least 12 continuous residues in the sequence of the dimerization region or DNA binding region of each E2F family) [simply referred to as "Compound I" hereinafter] or a pharmaceutically acceptable salt thereof. In accordance with the present invention, a pharmaceutical composition comprising the Compound (I) or a pharmaceutically acceptable salt thereof is provided.

In the definition of each group in the formula (I), the alkanoyl includes alkanoyl groups with 1 to 20 carbon atoms, such as formyl, acetyl, propionyl, butyryl, isobutyryl, valeryl, isovaleryl, pivaloyl, hexanoyl, heptanoyl, lauroyl, and icosanoyl.

The substituted alkanoyl has, the same or different, 1 to 3 substituents such as hydroxy, carboxyl, alicyclic alkyl, substituted or unsubstituted phenyl or fluorenyl.

Herein, the alicylic alkyl includes alicyclic alkyl groups with 3 to 8 carbon atoms, such as cyclopropyl, cyclobutyl, cyclopentyl, cyclohexyl, cycloheptyl, and cyclooctyl.

The substituted phenyl has, the same or different, 1 to 3 substituents such as alkyl, alkoxy, hydroxy, nitro, sulfo, cyano or halogen. The alkyl and the alkyl moiety of the alkoxy include alkyl groups with 1 to 20 carbon atoms, such as methyl, ethyl, propyl, isopropyl, butyl, pentyl, hexyl, heptyl, decyl, dodecyl, and icosyl; and the halogen includes each atom of fluorine, chlorine, bromine and iodine.

The aryl moiety of the aroyl and the aryloxycarbonyl includes e.g. phenyl and naphthyl. Each of the substituted aroyl and the substituted aryloxycarbonyl has, the same or different, 1 to 3 substituents such as alkyl, alkoxy, hydroxy, nitro, sulfo, or halogen. The alkyl and the alkyl moiety of the alkoxy and the halogen have the same meanings as defined above, respectively.

The heteroaryl moiety of the heteroarylcarbonyl and the heteroaryloxycarbonyl includes e.g., furyl, thienyl, pyridyl, pyrrolyl, pyrazolyl, pyrimidinyl, pyradinyl, indolyl, quinolyl, isoquinolyl, and quinazolyl. Each of the substituted heteroarylcarbonyl and the substituted heteroaryloxycarbonyl has the same substituents as defined for the substituents of the substituted aroyl.

The alkyl moiety of the alkoxycarbonyl and the alkoxy means the same as defined above. The substituents of the substituted alkoxycarbonyl and the substituted alkoxy include e.g. hydroxy, carboxy, carbamoyl, alicyclic alkyl, substituted or unsubstituted phenyl and fluorenyl. The alicyclic alkyl and the substituent of the substituted phenyl mean the same as defined above, respectively.

The substituted amino has, the same or different, 1 to 2 substituents such as substituted or unsubstituted alkyl, or substituted or unsubstituted aryl. The alkyl and the aryl have individually the same meanings as defined above. The substituents of the substituted alkyl include e.g. hydroxy, carboxy, carbamoyl, alicyclic alkyl and a phenyl group. The alicyclic alkyl has the same meaning as defined above. The substituted aryl has, the same or different, 1 to 3 substituents such as alkyl, alkoxy, hydroxy, nitro, sulfo or halogen. The alkyl and the alkyl moiety of the alkoxy, and the halogen have the same meanings as defined above, respectively.

In accordance with the present invention, the term "E2F" means a protein which binds to the E2F binding sequence in DNA and influences the promoter activity around the sequence. E2F is composed of the E2F family and DP family, and each family has a dimerization region and a DNA binding region. The sequences of the dimerization region and DNA binding region in each family of E2F are described in Cell, 70, 337 (1992); Cell, 70, 351 (1992); Mol. Cell. Biol., 13, 7802 (1993); Mol. Cell. Biol., 13, 7813 (1993); Genes and Dev., 8, 2680 (1994); Genes and Dev., 8, 2665 (1994); Proc. Natl. Acad. Sci. USA., 92, 2403 (1995); Nature, 362, 83 (1993); Mol. Cell. Biol., 15, 2536 (1995) and the like.

The peptide sequence comprising a partial amino acid sequence having at least 12 continuous residues in the sequence of the dimerization region of the E2F includes SEQ ID NO:25, e.g., a sequence represented by the general formula (Ia);

$$(X^1)n - (X^2)n - (X^3)n - (Ala)n - (X^5)n -$$
$$(X^6)n - (X^7)n - (X^8)n - (X^9)n - Val -$$
$$Gln - Lys - Arg - Arg - Ile -$$
$$Tyr - Asp - Ile - Thr - Asn -$$
$$Val - (Leu)n - (Glu)n - (Gly)n - (Ile)n -$$
$$(X^{26})n - (X^{27})n - (X^{28})n - (X^{29})n - \quad (Ia)$$

(wherein "n's in individual amino acid residues are the same or different, and represent 0 or 1; $X^1$, $X^8$, $X^{27}$ and $X^{28}$ are the same or different, representing Leu or Ile; $X^2$ represents Asn or Lys; $X^3$ represents Trp, Lys, Leu, Ala or Glu; $X^5$ represents Ala or Ser; $X^6$ represents Glu, Asp or Asn; $X^7$ represents Val, Thr or Arg; $X^9$ represents Lys, Asp, Ala or His; $X^{26}$ represents Gln, His, Gly, Asp or Asn; and $X^{29}$ represents Ala, Arg, Lys or Glu), and SEQ ID NO: 26, e.g., a sequence represented by the general formula (Ib);

$$(Y^1)m - (Y^2)m - (Y^3)m - (Gln) - (Y^5)m -$$
$$(Y^6)m - (Asp)m - (Gln)m - (Y^9)m - (Asn)m -$$
$$Ile - Arg - Arg - Arg - Val -$$
$$Tyr - Asp - Ala - Leu - Asn -$$
$$Val - Leu - Met - Ala - Y^{25} -$$
$$(Asn)m - (Y^{27})m - (Ile)m - (Ser)m - \quad (Ib)$$

(wherein "m's" in individual amino acid residues are the same or different, and represent 0 or 1; $Y^1$ represents Asn, Thr, Ala or Tyr; $Y^2$ represents Glu or Asp; $Y^3$ represents Ser or Asn; $Y^5$ represents Ala or Asn; $Y^6$ represents Tyr or Cys; $Y^9$ represents Lys or Glu; Y25 represents Met or Ile; and $Y^{27}$ represents Ile or Val.)

The peptide sequence comprising a partial amino acid sequence having at least 12 continuous residues in the sequence of the DNA binding region of the E2F includes SEQ ID NO: 27, e.g. a sequence represented by the general formula (Ic);

$$(Z^1)p - (Z^2)p - (Z^3)p - (Z^4)p - (Z^5)p -$$
$$(Z^4)p - (Z^7)p - (Z^8)^1 )p - (^{Z9})p - (Z^{10})p -$$
$$(Z^{11}p - (Z^{12})p - (Z^{13})p - (Z^{14})p - (Z^{15})p -$$
$$(Z^{16})p - (Z^{17})p - (Z^{18})p - (Z^{19})p - (Z^{20})p -$$
$$(Z^{21})p - (Z^{22})p - (Z^{23})p - (Z^{24})p - (Z^{25})p -$$
$$Arg - Z^{27} - Z^{28} - Z^{29} - Ser -$$
$$Leu - Z^{37} - Phe - Z^{39} - Z^{40} -$$
$$Z^{36} - Z^{37} - Phe - Z^{39} - Z^{40} -$$
$$Leu - \quad (Ic)$$

(wherein "p's" in individual amino acid residues are the same or different, and represent 0 or 1; $Z^1$ represents Ala, Phe or Pro; $Z^2$ represents Arg, Lys or Gln; $Z^3$, $Z^{15}$ and $Z^{21}$ are the same or different, representing Gly or Pro; $Z^4$ represents Arg, Lys, Met or Pro; $Z^5$ represents Gly, Cys, Ala or Gln; Z6 represents Ala, Arg or Glu; $Z^7$ represents Ala, Ile or Gln; $Z^8$ represents Ala, Gly or Arg; Z9 represents Leu, Val or Pro; $Z^{10}$ represents Asp, Arg or Gln; $Z^{11}$ represents Gly, Ser, Ala or Pro; $Z^{12}$ represents Leu or Pro; $Z^{13}$ represents Asp, His or Pro; $Z^{14}$ represents Ser or Pro; $Z^{16}$ represents Gln or Lys; $Z^{17}$ represents Gly, Thr or Leu; $Z^{18}$ represents Gly, Pro or Val; $Z^{19}$ represents Gly or Lys; $Z^{20}$ represents Ala or Ser; $Z^{22}$ represents Gly or Ser; Z23 represents Gly, Glu or Thr; $Z^{24}$ represents Arg, Lys, Ser or Pro; $Z^{25}$ represents Ser or Thr; $Z^{27}$ represents His or Tyr; $Z^{28}$ represents Asp or Glu; $Z^{29}$ and $Z^{36}$ are the same or different, representing Lys or Thr; $Z^{32}$ represents Gly or Asn; $Z^{34}$ represents Leu or Thr; $Z^{37}$ represents Arg or Lys; $Z^{39}$ represents Ile, Leu or Val; and $Z^{40}$ represents Glu, Gln, Ser or Tyr)

The pharmaceutically acceptable salt of the Compound (I) includes acid addition salts, metal salts, organic base addition salts and the like. The acid addition salts include inorganic salts such as hydrochloride, sulfate and phosphate; and organic salts such as acetate, maleate, fumarate, tartrate, and citrate. The metal salts include alkali metal salts such as sodium salt and potassium salt; alkaline earth metal salts such as magnesium salt and calcium salt; aluminium salt, zinc salt and the like. The organic base addition salts include salts of primary amines such as methylamine, ethylamine and aniline; secondary amines such as dimethylamine, diethylamine, pyrrolidine, piperidine, morpholine and piperazine; and tertiary amines such as trimethylamine, triethylamine, N,N-dimethylaniline and pyridine; and ammonium salts.

The present invention will now be described in. detail hereinbelow.

The abbreviations of amino acids and the protective groups thereof follow the recommendations by IUPAC-IUB Joint Commission on Biochemical Nomenclature [Eur. J. Biochem., 138, 9 (1984)].

The following abbreviations represent the following corresponding amino acids and protective groups thereof, unless otherwise stated.

Gly; Glycine
Ala; L-Alanine
Thr; L-Threonine
Asp; L-Aspartic acid
Asn; L-Asparagine
Asx; L-Aspartic acid or L-asparagine
Glu; L-Glutamic acid
Gln; L-Glutamine
Glx; L-Glutamic acid or L-glutamine
Trp; L-Tryptophan
Val; L-Valine
Leu; L-Leucine
Ser; L-Serine
Met; L-Methionine
Ile; L-Isoleucine
Phe; L-Phenylalanine
Tyr; L-Tyrosine
Lys; L-Lysine
Arg; L-Arginine
His; L-Histidine
Pro; L-Proline
Fmos; 9-Fluorenylmethyloxycarbonyl
t-Bu; t-Butyl
Trt; Trityl
Pmc; 2, 2, 5, 7, 8-Pentamethylchroman-6-sulfonyl Boc; t-Butyloxycarbonyl
Ac; Acetyl.

The following abbreviations represent the corresponding side-chain-protected amino acids as follows.

Fmoc-Asp(Ot-Bu)-OH; $N^\alpha$-9-Fluorenylmethyloxycarbonyl-L-aspartic acid β-t-butylester Fmoc-Glu(Ot-Bu)-OH; $N^\alpha$-9-Fluorenylmethyloxycarbonyl-L-glutamic acid γ-t-butylester Fmoc-Thr(Ot-Bu)-OH; $N^\alpha$-9-Fluorenylmethyloxycarbonyl-O-t-butyl-L-threonine Fmoc-Ser(t-Bu)-OH; $N^\alpha$-9-Fluorenylmethyloxycarbonyl-O-t-butyl-L-serine Fmoc-Tyr(t-Bu)-OH; $N^\alpha$-9-Fluorenylmethyloxycarbonyl-O-t-butyl-L-tyrosine Fmoc-Lys(Boc)-OH; $N^\alpha$-9-Fluorenylmethyloxycarbonyl-$N^\epsilon$-t-butyloxycarbonyl-L-lysine Fmoc-Asn(Trt)-OH; $N^\alpha$-9-Fluorenylmethyloxycarbonyl-$N^\gamma$-trityl-L-asparagine Fmoc-Gln(Trt)-OH; $N^\alpha$-9-Fluorenylmethyloxycarbonyl-$N^\delta$-trityl-L-glutamine Fmoc-Arg(Pmc)-OH; $N^\alpha$-9-Fluorenylmethyloxycarbonyl-$N^g$-2,2,5,7,8-pentamethylchroman-6-sulfonyl-L-arginine Fmoc-His(Trt)-OH; $N^\alpha$-9-Fluorenylmethyloxycarbonyl-$N^{im}$-trityl-L-glutamine Fmoc-Trp(Boc)-OH; $N^\alpha$-9-Fluorenylmethyloxycarbonyl-$N^{ind}$-t-butyloxycarbonyl-L-tryptophane The following abbreviations represent the corresponding reaction solvents and reaction reagents and the like as follows.

PyBOP; Benzotriazol-1-yloxytrispyrrolidinophosphonium hexafluorophosphate
HOBt; 1-Hydroxybenzotriazole
NMM; N-Methylmorpholine
DMF; N,N-Dimethylformamide
TFA; Trifluoroacetic acid
HBTU; 2-(1H-Benzotriazol-1-yl)-1,1,3,3-tetramethyluronium hexafluorophosphate
DIEA; N,N-Diisopropylethylamine
NMP; N-Methylpyrrolidone.

The method for producing the Compound (I) will now be described below.

The Compound (I) can be synthesized by general liquid phase or solid phase peptide synthetic methods [Fundamentals and Experiments of Peptide Synthesis, Nobuo Izumiya et al., Maruzen (1985)] or a combination thereof. Furthermore, an automatic peptide synthesizer may be used. The peptide synthesis on a commercially available peptide synthesizer, e.g. a peptide synthesizer manufactured by Shimadzu Corporation, a peptide synthesizer manufactured by Applied BioSystems Inc., USA (ABI Inc.), and a peptide synthesizer manufactured by Advanced ChemTech Inc., USA (ACT Inc.) can be done by using $N^\alpha$-9-fluorenylmethyloxycarbonyl amino acids or $N^\alpha$-t-butyloxycarbonyl amino acids with an appropriately protected side chain, according to the synthetic programs for the individual peptide synthesizers.

The protected amino acid as the starting materials of the Compound (I) and carrier resin can be available from ABI Inc., Shimadzu Corporation, Kokusan Chemical Works Co., Ltd., Nova Biochem Co., Watanabe Chemical Industries, Ltd., ACT Inc. or Peptide Institute Inc.

The Compound (I) thus obtained can be purified by high-performance liquid chromatography (referred to as HPLC hereinbelow) by using reverse-phase silica gel columns such as C-4, C-8 or C-18 type, column chromatography such as gel filtration with partition resin, adsorption resin, ion exchange resin, silica gel, chemically modified silica gel, reverse-phase silica gel, alumina, diamatoceous earth or magnesium silicate, or thin-layer chromatography.

The pharmaceutically acceptable salt of the Compound (I) can be obtained in a conventional manner. More specifically, the acid addition salt or organic base addition salt of the Compound (I) can be obtaiend by dissolving the Compound (I) in an aqueous solution of an acid or an organic base corresponding thereto and then freeze-drying the solution. The metal salt of the Compound (I) can be obtained by dissolving the Compound (I) in an aqueous solution containing the corresponding metal ion and purifying the solution by gel filtration or by HPLC.

Specific examples of the Compound (I) are shown in Table 1. Specific examples of the compound being represented by the general formula (I) having the amino acid sequence represented by the general formula (Ia) include compounds represented by Sequence ID Nos.1, 2 and 20, which are referred to as Compounds Ia-1, Ia-2 and Ia-3, respectively. Specific examples of the compound being represented by the general formula (I) having the amino acid sequence represented by the general formula (Ib) include compounds represented by Sequence ID Nos.3, 4 and 21, which are referred to as Compounds Ib-1, Ib-2 and Ib-3, respectively. Specific examples of the compound being represented by the general formula (I) having the amino acid sequence represented by the general formula (Ic) include a compound represented by SEQ ID No.5. which is referred to as Compound Ic-1.

TABLE 1

| Compounds | Sequences |
|---|---|
| Ia-1 | Ac-Leu-Asn-Trp-Ala-Ala-Glu-Val-Leu-Lys-Val-Gin-Lys-Arg-Arg-Ile-Tyr-Asp-Ile-Thr-Asn-Val-Leu- Glu-Gly-Ile-Gin-Leu-Ile-Ala-$NH_2$ (SEQ ID No.1) |
| Ia-2 | Ac-Val-Leu-Lys-Val-Gln-Lys-Arg-Arg-Ile-Tyr-Asp-Ile-Thr-Asn-Val-$NH_2$ (SEQ ID No.2) |
| Ia-3 | La-Leu-Asn-Trp-Ala-Ala-Glu-Val-Leu-Lys-Val-Gin-Lys-Arg-Arg-Ile-Tyr-Asp-Ile-Thr-Asn-Val-Leu-Glu-Gly-Ile-Gln-Leu-Ile-Ala-$NH_2$ (SEQ ID No.20) |
| Ib-1 | Ac-Asn-Glu-Ser-Ala-Tyr-Asp-Gln-Lys-Asn-Ile-Arg-Arg-Arg-Val-Tyr-Asp-Ala-Leu-Asn-Val-Leu-Met-Ala-Met-Asn-Ile-Ile-Ser-$NH_2$ (SEQ ID No.3) |
| Ib-2 | Ac-Ile-Arg-Arg-Arg-Val-Tyr-Asp-Ala-Leu-Asn-Val-Leu-Met-Ala-Met-$NH_2$ (SEQ ID No.4) |
| Ib-3 | La-Asn-Glu-Ser-Ala-Tyr-Asp-Gln-Lys-Asn-Ile-Arg-Arg-Arg-Val-Tyr-Asp-Ala-Leu-Asn-Val-Leu-Met-Ala-Met-Asn-Ile-Ile-Ser-$NH_2$ (SEQ ID No.21) |
| Ic-1 | Ac-Ala-Arg-Gly-Arg-Gly-Arg-His-Pro-Gly-Lys-Gly-Val-Lys-Ser-Pro-Gly-Glu-Arg-Ser-Arg-Tyr-Glu-Thr-Ser-Leu-Asn-Leu-Thr-Thr-Lys-Arg-Phe-Leu-Glu-Leu-$NH_2$ (SEQ ID No.5) |

In the table, Ac represents an acetyl group; and La represents a lauroyl group.

The biological activity of the Compound (I) is now described in test examples.

TEST EXAMPLE I

Assay of E2F-DNA Binding-inhibiting Activity by Gel Shift Assay (1-1) Expression of a Fusion Protein of E2F-1 and DP-1 in *Escherichia Coli*

So as to assay the activity to inhibit E2F-DNA binding, a fusion protein of glutathione-S-transferase (abbreviated as GST hereinbelow) with the genes of human E2F-1 [Cell, 70, 337 (1992); Cell, 70, 351 (1992)] and human DP-1 [Genes Dev., 7, 1850 (1993)] was prepared.

Firstly, gene sequences carrying the DNA binding regions and dimerization regions of human E2F-1 and DP-1 were individually obtained by RT-PCR [Reverse Transcription Polymerase Chain Reaction; PCR Technology, Erlich, H. A., ed., p.89–97, Stockton Press (1989)].

An expression plasmid for E2F-1 was constructed by the following method. By AGPC method [Acid Guanidium Thiocyanate-Phenol Chloroform; Anal. Biochem., 162, 156 (1987)], RNA was prepared from a human B cell line Jijoye (ATCC CCL87), which was then subjected to reverse transcription by using a kit manufactured by GIBCO-BRL, namely Super Script II kit, to prepare the cDNA. From the cDNA was recovered an objective cDNA fragment, by dividing the human E2F-1 cDNA into two regions by using the following two pairs of the combinations of oligonucleotide primers;

5'-AGAGAGAAGCTTAAAGCGTCATGGCCTTGG-CCGGGG CC-3'(38-mer; SEQ ID No.6) and

5'-TTCTGCACCTTCAGCACCTCGGCAGC-3'(26-mer; SEQ ID No.7) [N terminus]; as well as

5'-ACCAAGCGCTTCCTGGAGCTGCTGAG-3'(26-mer; SEQ ID No.8) and

5'-GGAAACCCTGGTACCTCCAAGCCCTG-3'(26-mer; SEQ ID No.9) [C terminus], amplifying the two regions by using AmpliTaq® Taq polymerase and DNA thermal cycler 480 [Perkin Elmer Cetus Co.] according to PCR (polymerase chain reaction) [Science, 239, 487 (1988)] and ligating the resulting two regions by using an inner SalI cleavage site. The resulting cDNA was cleaved with RsaI, to recover an RsaI (431)–RsaI (815) fragment [numerical figures in parentheses correspond to the base numbers in Cell, 70, 337 (1992)] of 338 base pairs. The DNA fragment was inserted into the SmaI cleavage site of plasmid pGEX-5X [manufactured by Pharmacia Co.] inserted with the N terminal region of GST downstream of the Tac promoter, to recover plasmid pGST-E2F-1 expressing a fusion protein of a part of human E2F-1 (101-st to 227-th amino acid residues from the N terminus) and GST.

An expression plasmid for DP-1 was constructed by the following method. By the same method as described above, RNA and cDNA were prepared from a human B cell line DND-39 (Fujizaki Cell Center, Hayashibara Biochemical Research Institute). From the cDNA was amplified a DNA fragment carrying a part of the human DP-1 cDNA, by PCR with the following two oligonucleotide primers individually having BamHI and EcoRI cleavage sequences at 5' terminus;

5'-CCACGGATCCCCAGCACTCACTTTGCCTCT-CAG-3'(33-mer; SEQ ID No.10) and

5'-CTGCGAATTCTACCGGTTTCTCTGCACCAGG-TTC-3'(34-mer, SEQ ID No.11).

The DNA fragment was cleaved with BamHI and EcoRI, to recover a BamHI-EcoRI fragment of 481 base pairs, which was then inserted into plasmid pGEX-3X (manufactured by Pharmacia, Co.) preliminarily cleaved with BamHI and EcoRI, to recover plasmid pGST-DP-1 expressing a fused protein of a part of the human DP-1 (84-th to 241-th amino acid residues from the N terminus) with GST. The nucleotide sequence of each of the two plasmids in the regions of E2F-1 and DP-1 was determined, and it was verified that the sequences were not modified at all, compared with the sequences in the references.

The two plasmids thus recovered, namely pGST-E2F-1 and pGST-DP-1, were introduced into an *Escherichia coli* XL1-blue [manufactured by Stratagene Co.] according to the method described in J. Mol. Biol., 166, 557(1983). Then, one platinum loop of each of the resulting transfection strains pGST-E2F-1/XL1-blue and pGST-DP-1/XL1-blue was inoculated on a Terrific broth [1.2% trypsin, 2.4% yeast extract, 0.4% glycerin, 0.1 M potassium hydrogen phosphate, pH 7.4] (40 ml) containing 50 μg/ml ampicillin in a 200-ml Erlenmeyer flask, for agitation culture at 30° C. overnight. Twenty milliliters of the culture solution were transferred into a 2-liter Erlenmeyer flask containing 400 ml of the same culture broth, for agitation culture at 30° C. Immediately when the absorbance of the culture solution at 600 nm reached 0.8, isopropyl-β-D-thiogalactoside [IPTG manufactured by Wako Pure Chemical Industries Co., Ltd.] was added to the culture solution to 0.1 mM, for culturing at 30° C. for another 4 hours. From the culture solution were collected bacteria cells by centrifugation, which were then rinsed in ice-cold physiological saline [PBS (phosphate buffered saline) containing 137 mM NaCl, 2.7 mM KCl, 8.1 mM $Na_2HPO_4$, and 1.5 mM $KH_2PO_4$] and were then suspended in 20 ml of PBS containing 0.1 mM phenylmethylsulfonyl fluoride [PMSF, manufactured by Sigma Co.]. The suspension was treated five times with ultrasonication for one minute, followed by addition of Triton X-100, Tween-20 and Sarcosyl to each final concentration of 1%, for subsequent gradual agitation at 4° C. for 60minutes. The treated solution was centrifuged to recover the supernatant, followed by addition of 400 μl of glutathione-Sepharose CL-4B (manufactured by Pharmacia Co.), prior to gradual agitation at 4° C. for 60 minutes. Through centrifugation, the precipitate was recovered, rinsed three times in PBS (5 ml) containing 0.1 mM PMSF, and eluted with 1.2ml of 50 mM Tris-HCl buffer (pH 8.0) containing 10 mM glutathione (manufactured by Wako Pure Chemical Industries Co., Ltd.), to recover objective fused proteins GST-E2F-1 and GST-DP-1.

(1-2) Gel Shift Experiments by Using GST-E2F-1 and GST-DP-1

The following two oligonucleotides including the E2F binding sequence, which are complementary sequences to each other;

5'-ATTTAAGTTTCGCGCCCTTTCTCAA-3'(25-mer; SEQ ID No.12) and

5'-TTGAGAAAGGGCGCGAAACTTAAAT-3'(25-mer; SEQ ID No.13)

were added individually at a concentration of 10 μM into a solution comprising 10 mM $MgCl_2$, 5 mM DTT and 50 mM Tris-HCl(pH 7.5), for treatment at 75° C. for 10 minutes, and the resulting solutions were left to stand at ambient temperature while gradually lowering the temperature for annealing. The resulting double-stranded DNA solution (10 μl) was kept in a reaction solution (30 μL) [50 mM Tris-HCl buffer(pH 7.5) containing 10 mM $MgCl_2$, 5 mM dithiothreitol (DTT) 10 units of T4 polynucleotide kinase (manufactured by TaKaRa), 0.2 mCi [γ-$^{32}$P]ATP (7,000 Ci/mmol ATP, manufactured by Amersham Co.)] at 37° C. for 60 minutes, to label the 5' terminus. By adding 0.5 M EDTA (2 μl) to the reaction solution, the reaction was terminated, and thereafter, unreactive [γ-$^{32}$P]ATP was removed by using a NickColumn G-50 (manufactured by Pharmacia Co.), to recover E2F probe. Into 20 mM HEPES buffer(pH 7.4)(20 μl) containing 40 mM KCl, 1 mM $MgCl_2$, 0.1 mM EDTA, 0.1% Nonidet P-40, and 1 mM DTT were added 0.1 pmol of $^{32}$P-labeled E2F probe, 100 ng of GST-E2F-1, 100 ng of GST-DP-1, 2 μg of calf thymus DNA and 0 to a 100 μM test compound, for reaction at 30° C. for 30 minutes. After the reaction, the reaction solution was electrophoresed by using 0.5×TBE [2.5 mM Tris-borate buffer, pH 8.3, 0.1 mM EDTA] as an electrophoresis buffer in 4% polyacrylamide gel. GST-E2F-1 and GST-DP-1 proteins were bound to the labeled E2F probe, so that the mobility thereof was reduced. Accordingly, the proteins were detected as upper bands. After electrophoresis, the gel was dried to assay the radioactivity in bands shifting upward, by using an image analyzer Type BAS2000 (manufactured by Fuji Film Co.). The radioactivity in each lane was assayed, to calculate the inhibition ratio, on the basis of the radioactivity of a sample with no test compound contained in the reaction system, according to the following equation.

Inhibition ratio=$(A-B)/A$

A: radioactivity in a band shifted in the absence of any test compound

B: radioactivity in a band shifted in the presence of a test compound.

TABLE 2

| Compounds | Concentration ($\mu$M) | Inhibition ratio (%) | IC$_{50}$ ($\mu$M) |
| --- | --- | --- | --- |
| Ia-1 | 1 | 29.7 | 2 |
|  | 10 | 92.5 |  |
|  | 100 | 86.5 |  |
| Ia-3 | 10 | 18.3 | 23 |
|  | 25 | 52.6 |  |
|  | 100 | 88.2 |  |
| Ib-1 | 1 | 13.7 | 10 |
|  | 10 | 52.9 |  |
|  | 100 | 87.6 |  |
| Ib-3 | 25 | 17.9 | 100 |
|  | 100 | 49.5 |  |

IC$_{50}$: compound concentration at which the inhibition ratio is 50%.

TEST EXAMPLE 2

Assay of Growth Inhibiting Activity on Saos-2 cell

1×10$^6$ cells of a human osteosarcoma-derived cell line Saos-2 (ATCC HTB85) cultured in an RPMI 1640 culture medium containing 10% fetal calf serum (manufactured by Nissui Co.; referred to as medium A hereinbelow) in the presence of 5% CO$_2$ at 37° C. were suspended in 50 $\mu$l of K-PBS buffer [137 mM KCl, 2.7 mM NaCl, 8.1 mM Na$_2$HPO$_4$, 1.5 mM KH$_2$PO$_4$, and 4 mM MgCl$_2$], followed by addition of a test compound appropriately diluted with K-PBS to a final concentration of 100 $\mu$M. The suspension was transferred on a 0.2-cm width cuvette (manufactured by BIO-RAD Laboratories) for loading an electric pulse (conditions: an electric voltage=3 kV/cm, a pulse width=100 $\mu$ seconds, a pulse interval=one second, a pulse number=two) by using a Shimadzu cell fusion system SSH-1 [manufactured by Shimadzu Corporation]. After leaving the cuvette to stand for 10 minutes, the cells were recovered and suspended in 3 ml of the medium A, for inoculation on a cell culture dish of a 60-mm diameter(manufactured by Iwaki Glass Co.). In the presence of 5% CO$_2$, the cells were cultured at 37° C. for 40 hours and were then peeled off by means of PBS containing 0.05% trypsin and 0.02% EDTA and dyed with 0.05% trypan blue, to count the number of viable cells by means of a modified Neubauer hemocytometry. Based on the cell number with no test compound under load of an electric pulse, the inhibition ratio was calculated by the following equation.

Inhibition ratio=$(A-B)/A$

A: viable cell number in the absence of any test compound

B: viable cell number in the presence of a test compound. The results are shown in Table 3.

TABLE 3

| Compounds | Inhibition ratio (%) |
| --- | --- |
| Ia-1 | 25 |
| Ib-1 | 73 |

TEST EXAMPLE 3

Assay of Activity Suppressing E2F Responsive Transcription (1)

The promoter sequence of human cdc2 gene [EMBO J., 11, 1797 (1992)], which has been reported to have an endogenous E2F responsive sequence and to effect an E2F dependent transcription, was bound to the upstream of the firefly luciferase gene, which was designated as reporter gene. The promoter region of the human cdc2 gene was cloned as follows. By using the following two oligonucleotides primers;

5 '-CTATACACTCCTAACCCTAAGTATTAGAAG-3' (30-mer; SEQ ID No.14) and

5'-AGCTACAACAACGCGTCGCTCTCCGCTC-3'(28-mer; SEQ ID No.15), 466-bp DNA in the human cdc2 promoter region was amplified from human genome DNA [Clontech Laboratories Inc.] by PCR as described above. The DNA fragment was cloned into a PCR product cloning vector pCRII [manufactured by Invitrogen Co.]. From the plasmid was cleaved a DNA fragment with restriction enzymes HindIII and XhoI, and the fragment was inserted into a HindIII-XhoI site of luciferase reporter vector pluc2 [Eur. J. Haematol., 52, 73 (1994)], to generate a reporter plasmid pcdc21uc2.

Two micrograms (2 $\mu$g) of the plasmid pcdc21uc2 thus prepared were introduced, together with a test compound (100 $\mu$M), into 1×10$^6$ cells of Saos-2 by electroporation, in the same manner as in the Test Example 2. As in the Test Example 2, the resulting cells were inoculated into a cell culture dish of a 60-mm diameter for culturing in the presence of 5% CO$_2$ at 37° C. for 40 hours, and thereafter, the cells were peeled off and recovered by centrifugation. The cells were suspended in 0.5 ml of a cell lysis buffer [1% Triton X-100, 100 mM KH$_2$PO$_4$(pH 7.8), 1 mM dithiothreitol] and centrifuged, to recover the supernatant, of which 200 $\mu$l was then used to assay the luciferase activity and of which 10 $\mu$l was used to assay the protein concentration. The luciferase activity was assayed as follows; 300 $\mu$l of a substrate solution [25 mM glycylglycine buffer(pH 7.8), 15 mM MgSO$_4$, 5 mM ATP, and 0.33 mM luciferin] was automatically injected into a luminometer LB953 (manufactured by Beltold Co.), to assay the luminescence for 10 seconds, which was defined as luciferase activity. The protein concentration was assayed with a protein assay kit (manufactured by BIO-RAD Laboratories), which was used to correct the luciferase activity. Based on the luciferase activity (after correction with protein concentration) of a sample with no test compound contained in the reaction system, the inhibition ratio was calculated by the following equation.

Inhibition ratio=$(A-B)/A$

A: luciferase activity in the absence of any test compound (after correction with protein concentration)
B: luciferase activity in the presence of a test compound (after correction with protein concentration).

The results are shown in Table 4.

TABLE 4

| Compounds | Inhibition ratio (%) |
|---|---|
| Ia-1 | 25 |
| Ib-1 | 83 |

TEST EXAMPLE 4

Assay of Activity Suppressing E2F Responsive Transcription (2)

(4-1) Construction of Reporter Cell Strain

Into the XhoI- and HindIII sites of luciferase reporter vector pluc2 with neomycin (G418) resistant gene [Eur. J. Haematol., 52, 73 (1994)] were inserted an SphI-HindIII fragment composed of the 200 base pairs in the core promoter region of the SV40 initial gene 128-0/5243-5171, base number according to "DNA Tumor Viruses, Molecular Biology of Tumor Viruses, 2nd Ed., Part 2 Revised, Edited by J. Tooze, Cold Spring Harbor Laboratory Press, 1982" and a fragment produced by annealing the following two synthetic oligonucleotides;

5'-TCGAGCCCGGGGGTACCGCATG-3'(22-mer; SEQ ID No.16) and

5'-CGGTACCCCCGGGC-3'(14-mer; SEQ ID No.17)

which fragment had XhoI and SphI sites at both the termini and had an SmaI and Asp718 (KpnI) sites, to create luciferase reporter vector pSE01uc2 for inserting a transcription regulatory region therein.

By then annealing together the following two oligonucleotides having an E2F responsive sequence inside and being complimentary to each other;

5'-TCGAGCTTGGCGGGAAACTTGGCGGGAAAC-TTGGCGGGAAACTTGGCGGGAAAGTCGACG-3' (60-mer; SEQ ID No.18) and 5'-GTACCGTCGACTTTCCCGCCAAGTTTCCCG-CCAAGTTTCCCGCCAAGTTTCCCGCCAAGC-3' (60-mer; SEQ ID No.19), and then inserting the annealed product into the XhoI and Asp718 sites of the constructed luciferase vector pSE01uc2, reporter plasmid pE2FII-1luc2 was constructed.

By the following method, the plasmid was introduced into a human osteosarcoma-derived cell strain Saos-2 (ATCC HTB85), and the resulting cell was defined as E2F responsive reporter cell. $2\times10^6$ cells of the Saos-2 cultured in the presence of 5% $CO_2$ in the medium A at 37° C. were suspended in K-PBS buffer (50 µl) [137 mM KCl, 2.7 mM NaCl, 8.1 mM $Na_2HPO_4$, 1.5 mM $KH_2PO_4$, 4 mM $MgCl_2$], followed by addition of 1 µg/µl plasmid pE2FII-1 luc2 (4 µg) prepared above. The suspension was transferred on a 0.2-cm width cuvette (manufactured by BIO-RAD Laboratories) for loading an electric pulse (conditions: an electric voltage=3 kV/cm, a pulse width=100 µ seconds, a pulse interval=one second, a pulse number=two) by using a Shimadzu cell fusion system SSH-1 [manufactured by Shimadzu Corporation] to introduce the gene by electroporation. After leaving the cuvette to stand for 10 minutes, the cells were recovered and suspended in 10 ml of the medium A, for inoculation on a cell culture dish of a 100-mm diameter (manufactured by Iwaki Glass Co.).

Twenty-four hours after the introduction of the gene, the medium was exchanged to medium A containing 0.2 mg/ml Geneticin® (G418 sulfate; manufactured by GIBCO BRL), to select clones with the introduced plasmid stably incorporated in the chromosome. On the fourteenth day after the introduction of the gene, clones having formed a single colony on the dish were separated by using a cloning cylinder. From the resulting clones were selected a reporter cell strain with response to E2F to induce luciferase activity, namely E2F-1/Saos-2-1, was recovered by using the response to the E2F-1 and RB introduction as a marker.

(4-2) Assay of Transcription Suppressing Activity

A test compound was introduced into the cell strain E2F-1/Saos-2-1 obtained above by using Lipofect AMINE™ (manufactured by GIBCO-BRL) described below, to assay the E2F dependent transcription suppressing activity as luciferase activity. $4\times10^5$ cells of E2F-1/Saos-2-1 were inoculated in the medium A in a 35-mm cell culture dish for culturing in the presence of 5% $CO_2$ at 37° C. for 24 hours. In 0.2ml of Opti-MEM®I medium (manufactured by GIBCO-BRL) were dissolved 3 µl of Lipofect AMINE™ and 1 or 10 nmol of a test compound, and the resulting solution was left to stand at ambient temperature for 15 minutes, followed by further addition of Opti-MEM™I medium (0.8 ml). From the cells was removed the solution, and then, the cells were rinsed in the Opti-MEM™I medium, to which was then added one milliliter of the solution, for culturing in the presence of 5% $CO_2$ at 37° C. for 6 hours (the final concentration of the test compound was 1 or 10 µM). Six hours later, one milliliter of the medium A was added to the culture, for another 48-hour culturing, and then, the cells were peeled off and recovered by centrifugation. The cells were suspended in a cell lysis buffer (0.5 ml) [1% Triton X-100, 100 mM $KH_2PO_4$(pH 7.8), 1 mM dithiothreitol] and were thereafter centrifuged to recover the supernatant. 200 µl of the supernatant was used to assay the luciferase activity, while 10 µl thereof was used to assay the protein concentration. The luciferase activity was assayed as follows; 300 µl of a, substrate solution [25 mM glycylglycine buffer(pH 7.8), 15 mM $MgSO_4$, 5 mM ATP, and 0.33 mM luciferin] was automatically injected into a luminometer LB953 (manufactured by Beltold Co.), to assay the luminescence for 10 seconds, which was defined as luciferase activity. The protein concentration was assayed with a protein assay kit (manufactured by BIO-RAD Laboratories), which was used to correct the luciferase activity. Based on the luciferase activity (after correction with the protein concentration) of a sample with no test compound contained in the reaction system, the inhibition ratio was calculated by the following equation.

Inhibition ratio=$(A-B)/A$

A: luciferase activity in the absence of any test compound (after correction with protein concentration)
B: luciferase activity in the presence of a test compound (after correction with protein concentration).

The results are shown in Table 5.

TABLE 5

| Compound | Concentration (μM) | Inhibition ratio (%) |
|---|---|---|
| Ic-1 | 1 | 17 |
|  | 10 | 28 |

TEST EXAMPLE 5

Growth Inhibition of Human Epidermoid Carcinoma Cell A431 and Human Colon Cancer Cell SW480

Human epidermoid carcinoma cell A431 (ATCC CRL-1555) or human colon cancer cell SW480 (ATCC CCL-228), preliminarily adjusted to 1×10$^4$ cells/ml in a DME culture medium (Nissui Co.) containing 10% fetal calf serum, was divided in a 0.1-ml portion into each well of a 96-well microtiter plate (Nunk Co., #167008). The cells were cultured in a $CO_2$ gas incubator at 37° C. for 24 hours, followed by addition of 0.05 ml of the test compound preliminarily diluted appropriately with the culture medium into each well, for subsequent culturing in a $CO_2$ gas incubator at 37° C. for 72 hours. After removing the culture supernatant, each well was rinsed in 0.15 ml of PBS buffer, followed by fresh addition of 0.05 ml of the culture medium into each well. The cell number in each well was counted by a cell proliferation kit II manufactured by Boehringer Mannheim Co. After adding 0.025 ml of colorimetric reagent to each well and keeping the plate in a $CO_2$ gas incubator at 37° C. for 3 hours, the absorbance at 490 nm and 655 nm was determined with a microplate reader Model 550 (manufactured by, BIO-RAD Laboratories), to calculate then the value (difference in absorbance) of the absorbance of each well at 490 nm (A490) minus the absorbance thereof at 655 nm (A655). Comparing the difference in absorbance between the non-treated cells and the cells treated with the test compound at the predetermined concentration, the cell growth inhibiting activity of the test compound at each concentration was calculated by the following equation.

Inhibition ratio=(A−B)/A

A: difference in absorbance in the absence of any test compound (A490–A655)

B: difference in absorbance in the presence of a test compound (A490–A655).

The results are shown in Table 6.

TABLE 6

| Compound | Concentration (μM) | Inhibition ratio (%) A431 cells | SW480 cells |
|---|---|---|---|
| Ia-3 | 33 | 21 | 41 |
| Ib-3 | 11 | 22 | 14 |
| Ib-3 | 33 | 42 | 44 |

The Compound (I) and the pharmaceutically acceptable salt thereof obtained in accordance with the present invention are useful as an anti-tumor agent or anti-arteriosclerosis agent and may satisfactorily be used as they are or at various dosing formulations. For example, the Compound (I) or the pharmaceutically acceptable salt thereof may be dissolved in physiological saline or an aqueous solution of glucose, lactose, mannitol or the like, and the resulting solution can be used as an appropriate pharmaceutical injection. For example, additionally, the Compound (I) or the pharmaceutically acceptable salt thereof is lyophilized, to which is added sodium chloride, to prepare a powdery injection. If needed, the pharmaceutical composition may contain additives well known in the pharmaceutical field, e.g. pharmaceutically acceptable salts.

The Compound (I) or the pharmaceutically acceptable salt thereof may be mixed and formulated with appropriate excipients, disintegrators, binders and lubricants, to prepare tablets, granules, powders and syrups in the form of oral agents. Still additionally, the Compound (I) or the pharmaceutically acceptable salt thereof may be mixed and formulated with routine carriers, to prepare suppositories, which may be administered into rectum.

The dose may vary, depending on the dosage route, the type of the Compound (I) or the pharmaceutically acceptable salt thereof, the age and conditions of a patient and the like, while the dosage route may also be variable, depending on the conditions and the dose. For example, the Compound (I) or the pharmaceutically acceptable salt thereof may be administered at 0.00001 to 100 mg/kg per day, preferably 0.001 to 10 mg/kg per day and more preferably 0.01 to 1 mg/kg per day.

BEST MODE FOR CARRYING OUT THE INVENTION

The present invention is now described in the following examples.

In the following examples, the physico-chemical properties of compounds were determined by the following methods. For mass analysis according to the FAB method, JEOL JMS-SX102A was used. Amino acid analysis was carried out according to the method of Bidlingmeyer et al. [J. Chromatogra., 336, 93 (1984)]. Hydrolysis was effected in the vapor of hydrochloric acid at 110° C. for 22 hours; and the amino acid composition of the hydrolysis product was analyzed by using an amino acid analyzer Pico Tag (manufactured by Waters Associates).

EXAMPLE 1

Synthesis of Compound Ia-1

($CH_3$-CO-Leu-Asn-Trp-Ala-Ala-Glu-Val-Leu-Ly s-Val-Gln-Lys-Arg-Arg-Ile-Tyr-Asp-Ile-Th r-Asn-Val-Leu-Glu-Gly-Ile-Gln-Leu-Ile-Al a-$NH_2$, SEQ ID No.1)

A carrier resin (30 mg) bonded with Fmoc-NH (14.1 μmol) (Rink Amide MBHA resin) was placed in the reactor of an automatic synthesizer, so as to practice the following procedures according to the synthesis program instructed by Shimadzu Corporation.

(a) The carrier resin was rinsed in DMF for 3 minutes, and then, the solution was discarded.

(b) After adding a 30% solution (900 μl) of piperidine in DMF to the resin, the resulting mixture was agitated for 4 minutes, and then, the solution was discarded. The procedure was repeated once more.

(c) The carrier resin was rinsed in DMF for one minute, and the solution was discarded. The procedure was repeated five times. In such manner, the Fmoc-removed carrier resin bonded with $NH_2$ was recovered.

(d) Fmoc-Ala-OH (70.5 μmol), PyBOP (70.5 μmol), HOBt monohydrate (70.5 μmol) and NMM (105.75 μmol) were agitated together in DMF (246.8 μl) for 3 minutes, and the resulting solution was added to the carrier resin. Then, the resulting mixture was agitated for 30 minutes, from which the solution was discarded.

(e) The carrier resin was rinsed in DMF for one minute, and the procedure was repeated five times. In such manner, Fmoc-Ala-NH was synthesized on the carrier resin.

After the procedures (a) to (c) for rinsing and deprotection, condensation reaction was carried out by using Fmoc-Ile-OH at the process (d), and through the rinse process (e), Fmoc-Ile-Ala was synthesized on the carrier resin. By subsequently using the following compounds at the process (d) and repeating the processes (a) to (e), a carrier resin bonded with protective peptide was recovered;

Fmoc-Leu-OH, Fmoc-Gln(Trt)-OH, Fmoc-Ile-OH, Fmoc-Gly-OH, Fmoc-Glu(Ot-Bu)-OH, Fmoc-Leu-OH, Fmoc-Val-OH, Fmoc-Asn(Trt)-OH, Fmoc-Thr (t-Bu)-OH, Fmoc-Ile-OH, Fmoc-Asp(Ot-Bu)-OH, Fmoc-Tyr(t-Bu)-OH, Fmoc-Ile-OH, Fmoc-Arg(P mc)-OH, Fmoc-Arg(Pmc)-OH, Fmoc-Lys(Boc)-OH, Fmoc-Gln(Trt)-OH, Fmoc-Val-OH, Fmoc-Lys(Bo c)-OH, Fmoc-Leu-OH, Fmoc-Val-OH, Fmoc-Glu(O t-Bu)-OH, Fmoc-Ala-OH, Fmoc-Ala-OH, Fmoc-Tr p-OH, Fmoc-Asn (Trt)-OH, and Fmoc-Leu-OH.

After further rising and deprotection processes (a) to (c), 50% acetic anhydride-containing DMF (1 ml) was added to the carrier resin, and the resulting mixture was agitated for 30 minutes. Then, the solution was discarded. The carrier resin was rinsed in DMF for one minute, the procedure was repeated five times, followed by sequential rinsing in methanol and butyl ether and drying under reduced pressure for 12 hours, and a carrier resin bonded with the peptide with a side-chain protective group was recovered. To the resin was added a mixture solution (800 µl) composed of 82.5% of TFA, 5% of thioanisole, 5% of water, 3% of ethyl methyl sulfide, 2.5% of 1,2-ethanedithiol and 2% of thiophenol and containing 2-methylindole at a ratio of 5 mg/ml, and the resulting mixture was left to stand at ambient temperature for 6 hours, to remove the side-chain protective groups and cleave the peptide from the carrier resin. After filtering off the carrier resin, about 10 ml of ether was added to the resulting solution. Through centrifugation and decantation, the generated precipitate was recovered as 39.1 mg of a crude peptide. The crude product was dissolved in 2M acetic acid, followed by HPLC purification on a reverse-phase column (CAPCELL PAK C18 of 30 mm I.D.×250 mm; manufactured by Shiseido, Co., Ltd.). The peptide was eluted on a linear gradient of 0.1% TFA–90% acetonitrile containing 0.1% TFA, as prepared by adding an aqueous 90% acetonitrile solution containing 0.1% TFA into an aqueous 0.1% TFA solution. The peptide was detected at 220 nm. Thus, a fraction containing the entitled compound was recovered. By lyophilizing the fraction, 7.5mg of Compound Ia-1 was recovered.

Mass spectrum [FABMS]; 3406 (M+H) Amino acid analysis; Asx2. 7 (3), Glx4. 4 (4), Gly1. 3 (1) Arg1. 8 (2) Thr0. 8 (1) Ala3. 5 (3), Tyr0. 9 (1), Val2. 6 (3) Ile3. 7 (4), Leu4. 1 (4), Lys2. 1 (2); Trp not determined.

EXAMPLE 2

Synthesis of Compound Ia-2

($CH_3$-CO-Val-Leu-Lys-Val-Gln-Lys-Arg-Arg-Il e-Tyr-Asp-Ile-Thr-Asn-Val-$NH_2$, SEQ ID No.2)

In the same manner as in Example 1, a carrier resin (30 mg) bonded with 14.7 µmol of Fmoc-NH as a starting material was condensed sequentially with Fmoc-Val-OH, Fmoc-Asn (Trt)-OH, Fmoc-Thr (t-Bu)-OH, Fmoc-Ile-OH, Fmoc-Asp (Ot-Bu)-OH, Fm oc-Tyr (t-Bu)-OH, Fmoc-Ile-OH, Fmoc-Arg (Pmc)-OH, Fmoc-Arg (Pmc)-OH, Fmoc-Lys (Boc)-OH, Fm oc-Gln (Trt)-OH, Fmoc-Val-OH, Fmoc-Lys (Boc)-OH, Fmoc-Leu-OH, and Fmoc-Val-OH.

As in Example 1, through the reaction with acetic anhydride followed by rinsing and drying, a carrier resin bonded with a side-chain protected peptide was recovered, into which was added a mixture solution (800 µl) of 82.5% of TFA, 5% of thioanisole, 5% of water, 3% of ethyl methyl sulfide, 2.5% of 1,2-ethanedithiol and 2% of thiophenol. The resulting mixture was left to stand at ambient temperature for 8 hours, to remove the side-chain protective groups and cleave the peptide from the carrier resin. As in Example 1, 40.7 mg of a crude peptide was recovered, followed by HPLC purification on a reverse-phase column, to recover 20.1 mg of Compound Ia-2.

Mass spectrum [FABMS]; 1885 (M+H) Amino acid analysis;

Asx1. 9 (2), Glx1. 1 (1), Arg2. 1 (2), Thr1. 0 (1) Tyr1. 0 (1), Val3. 0 (3), Ile2. 0 (2), Leu1. 0 (1) Lys1. 9 (2)

EXAMPLE 3

Synthesis of Compound Ib-1

($CH_3$-CO-Asn-Glu-Ser-Ala-Tyr-Asp-Gln-Lys-As n-Ile-Arg-Arg-Arg-Val-Tyr-Asp-Ala-Leu-As n-Val-Leu-Met-Ala-Met-Asn-Ile-Ile-Ser-$NH_2$. SEQ ID No.3)

In the same manner as in Example 1, a carrier resin (30 mg) bonded with 14.1 µmol of Fmoc-NH as a starting material was condensed sequentially with Fmoc-Ser (t-Bu)-OH, Fmoc-Ile-OH, Fmoc-Ile-O H, Fmoc-Asn (Trt)-OH, Fmoc-Met-OH, Fmoc-Ala-OH, Fmoc-Met-OH, Fmoc-Leu-OH, Fmoc-Val-OH, F moc-Asn (Trt)-OH, Fmoc-Leu-OH, Fmoc-Ala-OH, Fmoc-Asp (Ot-Bu)-OH, Fmoc-Tyr (t-Bu)-OH, Fmo c-Val-OH, Fmoc-Arg (Pmc)-OH, Fmoc-Arg (Pmc)-OH, Fmoc-Arg (Pmc)-OH, Fmoc-Ile-OH, Fmoc-Asn (Trt)-OH, Fmoc-Lys (Boc)-OH, Fmoc-Gln (Trt)-OH, Fmoc-Asp (Ot-Bu)-OH, Fmoc-Tyr (t-Bu)-OH, Fmoc-Ala-OH, Fmoc-Ser (t-Bu)-OH, Fmoc-Glu (O t-Bu)-OH, and Fmoc-Asn (Trt)-OH.

As in Example 1, through the reaction with acetic anhydride followed by rinsing and drying, a carrier resin bonded with a side-chain protected peptide was recovered, into which was added a mixture solution (800 µl) of 82.5% of TFA, 5% of thioanisole, 5% of water, 3% of ethyl methyl sulfide, 2.5% of 1,2-ethanedithiol and 2% of thiophenol. The resulting mixture was left to stand at ambient temperature for 8 hours, to remove the side-chain protective groups and cleave the peptide from the carrier resin. As in Example 1, 34.7 mg of a crude peptide was recovered, followed by HPLC purification on a reverse-phase column, to recover 6.3 mg of Compound Ib-1.

Mass spectrum [FABMS]; 3337 (M+H) Amino acid analysis;

Asx6. 4 (6), Glx2. 4 (2) Ser2. 4 (2), Arg2. 5 (3) Ala3. 6 (3), Tyr2. 2 (2) Val1. 5 (2) Met2. 1 (2) Ile2. 0 (3), Leu1. 7 (2), Lys1. 2 (1)

EXAMPLE 4

Synthesis of Compound Ib-2

($CH_3$-CO-Ile-Arg-Arg-Arg-Val-Tyr-Asp-Ala-Le u-Asn-Val-Leu-Met-Ala-Met-$NH_2$, SEQ ID No.4)

In the same manner as in Example 1, a carrier resin (30 mg) bonded with 14.7 µmol of Fmoc-NH as a starting material was condensed sequentially with Fmoc-Met-OH, Fmoc-Ala-OH, Fmoc-Met-OH, Fmoc-Leu-OH, Fmoc-Val-OH, Fmoc-Asn(Trt)-OH, Fmoc-Leu-OH, Fmoc-Ala-OH, Fmoc-Asp(Ot-Bu)-OH, Fmoc-Tyr (t-Bu)-OH, Fmoc-Val-OH, Fmoc-Arg(P mc)-OH, Fmoc-Arg(Pmc)-OH, Fmoc-Arg(Pmc)-OH, and Fmoc-Ile-OH.

As in Example 1, through the reaction with acetic anhydride followed by rinsing and drying, a carrier resin bonded with a side-chain protected peptide was recovered, into which was added a mixture solution (800 µl) of 82.5% of TFA, 5% of thioanisole, 5% of water, 3% of ethyl methyl sulfide, 2.5% of 1,2-ethanedithiol and 2% of thiophenol. The resulting mixture was left to stand at ambient temperature for 8 hours, to remove the side-chain protective groups and cleave the peptide from the carrier resin. As in Example 1, 29.0 mg of a crude peptide was recovered, followed by HPLC purification on a reverse-phase column, to recover 5.9mg of Compound Ib-2.

Mass spectrum [FABMS]; 1861 (M+H) Amino acid analysis;
  Asx2. 0 (2), Arg 3. 0 (3), Ala2. 1 (2),Tyr1. 0 (1) Val1. 8 (2), Met2. 1 (2), Ile1. 0 (1), Leu2. 0 (2)

EXAMPLE 5

Synthesis of Compound Ic-1

($CH_3$-CO-Ala-Arg-Gly-Arg-Gly-Arg-His-Pro-Gl y-Lys-Gly-Val-Lys-Ser-Pro-Gly-Glu-Arg-Se r-Arg-Tyr-Glu-Thr-Ser-Leu-Asn-Leu-Thr-Th r-Lys-Arg-Phe-Leu-Glu-Leu-$NH_2$, SEQ ID No.5)

In the same manner as in Example 1, a carrier resin (20 mg) bonded with 9.8 pnol of Fmoc-NH as a starting material was condensed sequentially with Fmoc-Leu-OH, Fmoc-Glu(Ot-Bu)-OH, Fmoc-Leu-OH, Fmoc-Phe-OH, Fmoc-Arg(Pmc)-OH, Fmoc-Lys(Boc)-OH, Fmoc-Thr(t-Bu)-OH, Fmoc-Thr (t-Bu)-OH, Fmoc-Leu-OH, Fmoc-Asn(Trt)-OH, Fmoc-Le u-OH, Fmoc-Ser(t-Bu)-OH, Fmoc-Thr(t-Bu)-OH, Fmoc-Glu (Ot-Bu)-OH, Fmoc-Tyr(t-Bu)-OH, Fmo c-Arg(Pmc)-OH, Fmoc-Ser(t-Bu)-OH, Fmoc-Arg (Pmc)-OH, Fmoc-Glu(Ot-Bu)-OH, Fmoc-Gly-OH, Fmoc-Pro-OH, Fmoc-Ser(t-Bu)-OH, Fmoc-Lys(B oc)-OH, Fmoc-Val-OH, Fmoc-Gly-OH, Fmoc-Lys(B oc)-OH, Fmoc-Gly-OH, Fmoc-Pro-OH, Fmoc-His(T rt)-OH, Fmoc-Arg (Pmc)-OH, Fmoc-Gly-OH, Fmoc-Arg(Pmc)-OH, Fmoc-Gly-OH, Fmoc-Arg(Pmc)-O H, and Fmoc-Ala-OH.

As in Example 1, through the reaction with acetic anhydride followed by rinsing and drying, a carrier resin bonded with a side-chain protected peptide was recovered, into which was added a mixture solution (800 µl) of 82.5% of TFA, 5% of thioanisole, 5% of water, 3 t of ethyl methyl sulfide, 2.5% of 1,2-ethanedithiol and 2% of thiophenol. The resulting mixture was left to stand at ambient temperature for 8 hours, to remove the side-chain protective groups and cleave the peptide from the carrier resin. As in Example 1, 38.7 mg of a crude peptide was recovered, followed by HPLC purification on a reverse-phase column, to recover 5.6mg of Compound Ic-1.

Mass spectrum [FABMS]; 3993 (M+H) Amino acid analysis;
  Asx1. 1 (1), Glx3. 0 (3), Ser2. 6 (3), Gly5. 6 (5), His1. 1 (1), Arg5. 0 (6), Thr2. 9 (3), Ala1. 0 (1), Pro2. 2 (2), Tyr0. 8 (1), Val0. 9 (1), Leu4. 4 (4), Phe1. 0 (1), Lys3. 2 (3)

EXAMPLE 6

Synthesis of Compound Ia-3

[$CH_3$-$(CH_2)_{10}$-CO-Leu-Asn-Trp-Ala-Ala-Glu-Val-L eu-Lys-Val-Gln-Lys-Arg-Arg-Ile-Tyr-Asp-I le-Thr-Asn-Val-Leu-Glu-Gly-Ile-Gln-Leu-I le-Ala-$NH_2$, SEQ ID No.20].

A carrier resin (100 mg)-bonded with 20 µmol of Fmoc-NH (NovaSyn TGR Resin; manufactured by Nova Biochem, Co.) as a starting material was subjected to the following procedures by using a peptide synthesizer manufactured by ACT Inc.

(a) The carrier resin was rinsed in DMF (1 ml) under agitation for 3 minutes, and then, the solution was discarded. The procedure was repeated twice.

(b) After adding a 25% solution (1 ml) of piperidine in DMF to the resin, the resulting mixture was agitated for 2 minutes, and then, the solution was discarded. After adding again the 25% solution (1 ml) of piperidine in DMF to the resin, the resulting mixture was further agitated for 10 minutes, and then, the solution was discarded.

(c) The carrier resin was rinsed in DMF (1 ml) under agitation for one minute, and the solution was discarded. The procedure was repeated seven times.

In such manner, a carrier resin from which any Fmoc group was removed was recovered.

(d) DMF (250 µl), an NMP solution (500 µl) containing Fmoc-Ala-OH and HOBt monohydrate, individually at a concentration of 0.5 M, and an NMP solution containing DIC at a concentration of 0.5 M, were added to the resin, for 45-min agitation, and then, the solution was discarded.

(e) The carrier resin was rinsed in DMF (1 ml) under agitation for one minute, and then, the resin was again rinsed in DMF (1 ml).

(f) DMF (250 µl), an NMP solution (500 µl) containing Fmoc-Ala-OH and HOBt monohydrate, individually at a concentration of 0.5 M, a DMF solution (500 µl) containing HBTU at a concentration of 0.5 M, and an NMP solution (250 µl) containing DIEA at a concentration of 2 M were added to the resin, for 30-min agitation, and then, the solution was discarded.

(g) The procedure (e) was repeated twice.

In such manner, Fmoc-Ala-NH was synthesized on the carrier resin.

After the procedures (a) to (c) for rinsing and deprotection, condensation reaction was carried out by using a solution containing Fmoc-Ile-OH instead of Fmoc-Ala-OH at the processes (d) and (f), and through the rinse processes (e) and (g), Fmoc-Ile-Ala-NH was synthesized on the carrier resin. By subsequently using the following compounds at the processes (d) and (f) and repeating the processes (a) to (g), a carrier resin bonded with a protective peptide was recovered;

Fmoc-Leu-OH, Fmoc-Gln(Trt)-OH, Fmoc-Ile-OH, Fmoc-Gly-OH, Fmoc-Glu(Ot-Bu)-OH, Fmoc-Leu-OH, Fmoc-Val-OH, Fmoc-Asn(Trt)-OH, Fmoc-Thr (t-Bu)-OH, Fmoc-Ile-OH, Fmoc-Asp(Ot-Bu)-OH, Fmoc-Tyr(t-Bu)-OH, Fmoc-Ile-OH, Fmoc-Arg(P mc)-OH, Fmoc-Arg(Pmc)-OH, Fmoc-Lys(Boc)-OH, Fmoc-Gln(Trt)-OH, Fmoc-Val-OH, Fmoc-Lys(Bo c)-OH, Fmoc-Leu-OH, Fmoc-Val-OH, Fmoc-Glu(O t-Bu)-OH, Fmoc-Ala-OH, Fmoc-Ala-OH, Fmoc-Tr p(Boc)-OH, Fmoc-Asn (Trt)-OH, and Fmoc-Leu-O H.

After further rising and deprotection processes (a) to (c), a DMF solution (500 μl) containing 20 mg lauric acid, a DMF solution (500 μl) containing HBTU at a concentration of 0.5 M, and an NMP solution (250 μl) containing DIEA at a concentration of 2M were added to the resin, and the resulting mixture was agitated for 12 hours. Then, the solution was discarded. The carrier resin was rinsed and dried as in Example 1, to recover a carrier resin bonded with a side-chain protected peptide. To the above carrier resin was added a mixture solution (1200 μl) composed of 82.5% of TFA, 5% of thioanisole, 5% of water, 3% of ethyl methyl sulfide, 2.5% of 1,2-ethanedithiol, 2% of thiophenol and 2-methylindole (5 mg/ml), and the resulting mixture was left to stand at ambient temperature for 6 hours, to remove the side-chain protective groups and cleave the peptide from the carrier resin. In the same manner as in Example 1, 53.0 mg of a crude peptide was recovered, followed by HPLC purification on a reverse-phase column, to recover 5.3 mg of Compound Ia-3.

Mass spectrum [FABMS]; 3546 (M+H) Amino acid analysis;

Asx2. 8 (3), Glx4. 1 (4), Gly1. 3 (1), Arg2. 0 (2) Thr1. 0 (1), Ala3. 2 (3), Tyr1. 0 (1), Val2. 7 (3) Ile3. 9(4), Leu4. 0(4), Lys2. 0(2); Trp not determined.

EXAMPLE 7

Synthesis of Compound Ib-3

[$CH_3$-($CH_2$)$_{10}$-CO-Asn-Glu-Ser-Ala-Tyr-Asp-Gln-Lys-Asn-Ile-Arg-Arg-Arg-Val-Tyr-Asp-Ala-Leu-Asn-Val-Leu-Met-Ala-Met-Asn-Ile-Ile-Ser-$NH_2$, SEQ ID No.21].

In the same manner as in Example 6, a carrier resin (100 mg) bonded with 20 μmol of Fmoc-NH as a starting material was condensed sequentially with Fmoc-Ser(t-Bu)-OH, Fmoc-Ile-OH, Fmoc-Ile-O H, Fmoc-Asn(Trt)-OH, Fmoc-Met-OH, Fmoc-Ala-OH, Fmoc-Met-OH, Fmoc-Leu-OH, Fmoc-Val-OH, F moc-Asn(Trt)-OH, Fmoc-Leu-OH, Fmoc-Ala-OH, Fmoc-Asp(Ot-Bu)-OH, Fmoc-Tyr(t-Bu)-OH, Fmo c-Val-OH, Fmoc-Arg(Pmc)-OH, Fmoc-Arg(Pmc)-OH, Fmoc-Arg (Pmc)-OH, Fmoc-Ile-OH, Fmoc-Asn (Trt)-OH, Fmoc-Lys(Boc)-OH, Fmoc-Gln(Trt)-OH, Fmoc-Asp (Ot-Bu)-OH, Fmoc-Tyr (t-Bu)-OH, Fmoc-Ala-OH, Fmoc-Ser(t-Bu)-OH, Fmoc-Glu(O t-Bu)-OH, and Fmoc-Asn (Trt)-OH.

As in Example 6, through the reaction with lauric acid, followed by rinsing and drying, a carrier resin bonded with a side-chain-protected peptide was recovered, into which was added a mixture solution (1200 μl) of 82.5% of TFA, 5% of thioanisole, 5% of water, 3% of ethyl methyl sulfide, 2.5% of 1,2-ethanedithiol and 2% of thiophenol. The resulting mixture was left to stand at ambient temperature for 8 hours, to remove the side-chain protective groups and cleave the peptide from the carrier resin. As in Example 1, 47.9 mg of a crude peptide was recovered, followed by HPLC purification on a reverse-phase column, to recover 2.2 mg of Compound Ib-3.

Mass spectrum [FABMS]; 3477 (M+H) Amino acid analysis;

Asx5. 9 (6), Glx2. 0 (2), Ser2. 0 (2), Arg2. 9 (3) Ala3. 4 (3), Tyr2. 1 (2), Val1. 9 (2), Met2. 3 (2) Ile2. 2 (3), Leu2. 2 (2) Lys1. 1 (1)

Industrial Applicability

In accordance with the present invention, a novel compound inhibiting the E2F activity and having excellent anti-tumor activity or anti-arteriosclerosis activity can be provided. The compound is useful as a therapeutic agent of diseases such as tumor and arteriosclerosis, for which abnormal cell growth is responsible.

---

What is claimed is:

1. A compound represented by the formula (I):

   (I)

wherein $R^1$ represents substituted or unsubstituted alkanoyl, substituted or unsubstituted aroyl, substituted or unsubstituted heteroarylcarbonyl, substituted or unsubstituted alkoxycarbonyl, substituted or unsubstituted aryloxycarbonyl, or substituted or unsubstituted heteroaryloxycarbonyl;

$R^2$ represents substituted or unsubstituted alkoxy, or substituted or unsubstituted amino; and A represents a peptide sequence comprising 12 continuous residues in the sequence of the dimerization region or DNA binding region of each E2F family, or a pharmaceutically acceptable salt thereof.

2. A compound represented by the formula (I):

   (I)

wherein $R^1$ represents substituted or unsubstituted alkanoyl, substituted or unsubstituted aroyl, substituted or unsubstituted heteroarylcarbonyl, substituted or unsubstituted alkoxycarbonyl, substituted or unsubstituted aryloxycarbonyl, or substituted or unsubstituted heteroaryloxycarbonyl or a hydrogen atom;

$R^2$ represents hydroxy, substituted or unsubstituted alkoxy, or substituted or unsubstituted amino; and A represents a peptide sequence that is at least 12 continuous residues from the dimerization region or DNA binding region of each E2F family, with the proviso that said peptide sequence is not an intact protein which is a member of E2F family or DP family, or a pharmaceutically acceptable salt thereof.

3. A compound represented by the formula (I):

   (I)

wherein $R^1$ represents substituted or unsubstituted alkanoyl, substituted or unsubstituted aroyl, substituted or unsubstituted heteroarylcarbonyl, substituted or unsubstituted alkoxycarbonyl, substituted or unsubstituted aryloxycarbonyl, substituted or unsubstituted heteroaryloxycarbonyl or a hydrogen atom;

$R^2$ represents substituted or unsubstituted alkoxy, or substituted or unsubstituted amino; and A represents a peptide sequence comprising 12 continuous residues in the sequence of the dimerization region or DNA binding region of each E2F family, or a pharmaceutically acceptable salt thereof.

4. A compound represented by the formula (I):

   (I)

wherein $R^1$ represents substituted or unsubstituted alkanoyl, substituted or unsubstituted aroyl, substituted or unsubstituted heteroarylcarbonyl, substituted or unsubstituted alkoxycarbonyl, substituted or unsubstituted aryloxycarbonyl, or substituted or unsubstituted heteroaryloxycarbonyl;

$R^2$ represents hydroxy, substituted or unsubstituted alkoxy, or substituted or unsubstituted amino; and A represents a peptide sequence comprising 12 continuous residues in the sequence of the dimerization region or DNA binding region of each E2F family, or a pharmaceutically acceptable salt thereof.

5. A compound according to any one of claims 1, 2, 3, or 4, wherein A consists of:

—Asn-Glu-Ser-Ala-Tyr-Asp-Gln-Lys-Asn-Ile-Arg-Arg-Arg-Val-Tyr-Asp-Ala-Leu-Asn-Val-Leu-Met-Ala-Met-Asn-Ile-Ile-Ser-(SEQ ID NO:22)

or a pharmaceutically acceptable salt thereof.

6. A pharmaceutical composition comprising a compound or pharmaceutically acceptable salt according to any one of claims 1, 5 or 2–4, and a pharmaceutically acceptable carrier.

* * * * *